United States Patent [19]

Karn

[11] Patent Number: 4,627,928

[45] Date of Patent: Dec. 9, 1986

[54] BASIC NON-CARBONATED MAGNESIUM COMPOSITIONS AND FUEL, LUBRICANT AND ADDITIVE CONCENTRATE COMPOSITIONS CONTAINING SAME

[75] Inventor: Jack L. Karn, Richmond Hgts., Ohio

[73] Assignee: The Lubrizol Corporation, Wickliffe, Ohio

[21] Appl. No.: 761,296

[22] Filed: Jul. 29, 1985

Related U.S. Application Data

[63] Continuation of Ser. No. 267,441, May 27, 1981, abandoned, which is a continuation of Ser. No. 718,448, Aug. 26, 1976, abandoned, which is a continuation-in-part of Ser. No. 322,246, Jan. 9, 1973, abandoned, which is a continuation-in-part of Ser. No. 201,154, Nov. 22, 1971, abandoned.

[51] Int. Cl.$^4$ .................... C10M 179/26; C10L 1/32
[52] U.S. Cl. ........................................ 252/33; 252/18; 252/25; 252/33.2; 252/33.3; 252/39; 252/40.7; 44/51; 44/76
[58] Field of Search ................... 252/18, 25, 33, 33.2, 252/33.3, 39, 40.7; 44/51, 76

[56] References Cited

U.S. PATENT DOCUMENTS

| | | | |
|---|---|---|---|
| 2,616,904 | 11/1952 | Asseff et al. | 252/33 X |
| 2,744,069 | 5/1956 | Van Loon | 252/40.7 |
| 2,944,970 | 7/1960 | Peterson | 252/40.7 X |
| 2,951,808 | 9/1960 | Norton et al. | 252/18 |
| 2,961,404 | 11/1960 | Francis | 252/33.3 |
| 3,595,791 | 7/1971 | Cohen | 252/18 X |
| 3,625,893 | 12/1971 | Brook et al. | 252/39 X |
| 3,704,315 | 11/1972 | Strang | 252/39 X |
| 3,808,142 | 4/1974 | Crocker | 252/40.7 |
| 4,094,801 | 6/1978 | Forsberg | 252/39 X |

Primary Examiner—William R. Dixon, Jr.
Assistant Examiner—Cynthia A. Prezlock
Attorney, Agent, or Firm—Joseph P. Fischer; Denis A. Polyn; James L. Cordek

[57] ABSTRACT

This invention relates to basic magnesium salts of substituted aromatic hydroxy carboxylic acids or the derivatives thereof and to a process for preparing such salts. These salts can be used either along or in combination, as additives, in a variety of lubricating oils and fuels including gasoline, diesel fuels, etc.

44 Claims, No Drawings

BASIC NON-CARBONATED MAGNESIUM COMPOSITIONS AND FUEL, LUBRICANT AND ADDITIVE CONCENTRATE COMPOSITIONS CONTAINING SAME

REFERENCES TO RELATED APPLICATIONS

This is a continuation of co-pending application Ser. No. 267,441 filed on May 27, 1981, now abandoned, which is a continuation of Ser. No. 718,441 filed Aug. 26, 1976 now abandoned, which is a continuation-in-part of Ser. No. 322,246 filed Jan. 9, 1973, and now abandoned which in turn, is a continuation-in-part of Ser. No. 201,154 filed Nov. 22, 1971, and now abandoned.

This invention relates to basic magnesium salts of a substituted aromatic hydroxy-containing carboxylic composition and to a process for preparing said salts. More specifically, this invention is directed to a process for preparing basic magnesium salts of substituted aromatic hydroxy-containing carboxylic acids and to the products obtained therefrom and to their use as additives in a variety of lubricating oils and fuels, e.g., gasoline, diesel fuels, etc. The basic magnesium salts of the hydroxy-containing aromatic carboxylic acids are obtained by reacting at a temperature of at least about 25° C. at least one substantially hydrocarbon-substituted aromatic hydroxy-containing carboxylic acid or a derivative thereof with a stoichiometric excess of magnesium oxide, optionally in the presence of at least one sulfur-containing organic acid or its derivative, e.g., a sulfonic acid, etc., and at least about 0.1 mole of water and refluxing the reaction mixture thus formed for at least about 0.5 hour, preferably until it is substantially haze-free.

The present invention also includes the basic magnesium salts of the mono- and polycarboxylic aromatic hydroxy-containing carboxylic acids made by the inventive process and the use of these magnesium salts either alone or in combination as, e.g., dispersants, detergents or antioxidants in oils or fuels, etc., with other known additives.

Generally, it is known that the deterioration of a motor oil, for example, during the operation of an engine, causes the formation of sludge, varnish, etc., which ultimately obstructs the operation of the working parts. Presently, various dispersants, detergents and the like are used as additives in fuels and lubricants for gears, power-transmitting units internal combustion engines, etc. Although many of these materials have achieved widespread acceptance, there is still need for other additives which, for example, not only inhibit the deterioration of the motor oil under actual service conditions, but also improve the general lubricating characteristics of the oil.

As the use of basic metal salts as additives for fuels and motor oils, etc., increases, it becomes important to provide improved methods for preparing these metal salts, e.g., overbased magnesium sulfonates, carboxylates and the like. For example, the basic magnesium salts presently available are prepared by utilizing a stoichiometric excess of a magnesium compound in the presence of various promoters such as alcohols, phenols and the like together with an acidic material, e.g., carbon dioxide, to promote the overbasing of the acids. Obviously, it would be an advantage to have a process for preparing these basic magnesium compositions, e.g., an overbased magnesium carboxylate which does not rely on the use of an acidic material, e.g., carbon dioxide, etc., to facilitate the overbasing. It has, for example, been found that such non-carbonated basic magnesium salts are particularly useful in lubricants used in railroad diesel engines and as non-gas-forming stabilizers for polymers such as polyvinylchloride.

It has been found in accordance with this invention that a basic magnesium salt of a substantially hydrocarbon substituted, aromatic hydroxy-containing carboxylic acid can be obtained by utilizing a stoichiometric excess of a magnesium oxide in the presence of an effective amount of water and, optionally, in the presence of an effective amount of at least one sulfur-containing organic acid. These magnesium salts can be characterized as basic hydroxy-containing alkylated aromatic carboxylic acid salts having a magnesium content of at least 150% up to 500%, preferably 200%, most preferably 250% of the stoichiometrically equivalent amount of magnesium based on the amount of total acid present. The amount of total acid present can be determined by titration to the phenolphthalein end point.

It is the object of this invention to provide basic magnesium salts of alkylated aromatic hydroxy-containing carboxylic acids, e.g., alkyl-substituted hydroxy benzoic acids, which can be used as dispersants with oxidation-inhibiting characteristics in various lubricating oils and fuels. It is still a further object of this invention to provide compositions comprising a lubricating oil or normally liquid fuel containing effective amounts of basic magnesium salts of alkyl substituted hydroxy-containing aromatic carboxylic acids.

These and other objects can be accomplished by providing a process for preparing basic magnesium salts of substituted aromatic hydroxy-containing carboxylic compositions, e.g., alkyl-substituted hydroxy benzoic acids, such as a basic magnesium salt of a salicyclic acid, which comprises reacting at a temperature of about 25° C. up to the decomposition temperature of a reactant (A) at least one hydrocarbon-substituted or substantially hydrocarbyl-substituted aromatic hydroxy carboxylic acid, salt or saponifiable derivative thereof, wherein the substantially hydrocarbon substituent contains up to 10 weight percent of polar groups selected from the group consisting of mercapto, halogen, nitro, amino, nitroso, sulfur, keto, oxo groups and various combinations thereof, and; (B) a stoichiometric excess to about 15 equivalents of at least one basically reactive magnesium compound selected from the group consisting of magnesium oxides, hydroxides and alkoxides for each equivalent of said acid salt or derivative thereof, in the presence of (C) at least about 0.1 mole of water for each equivalent of magnesium compound, and then refluxing the resulting mixture for at least about 30 minutes, with the proviso that the reaction is carried out in the absence of any substantial amount of any carboxylic acid other than (A), optionally in the presence of (D) up to about 0.25 equivalent of at least one sulfur-containing organic acid or its derivative for each equivalent of said aromatic hydroxy-containing carboxylic acid or derivative thereof.

It is a significant feature of this invention that the non-carbonated, basic magnesium salts of this invention are formed in the absence of any substantial amount of inorganic acid material and, optionally, in the absence of any added organic acid other than (A) as defined herein. In this specification and the appended claims this means that there is not present any amount of such inorganic acidic material or acid which will deleteriously affect the final product, or which will cause the formation of products which are not described herein as having the optimum properties. What is substantial may vary in each case but the amount of such acid should be kept under that which will undesirably modify the final product.

In certain embodiments of this invention the reaction of (A), (B) and (C) is carried out in the absence of any substantial amount of acid material (organic or inorganic) other than (A).

The hydrocarbon-substituted hydroxy-containing aromatic acids, e.g., substantially aliphatic hydrocarbon substituted aromatic hydroxy-containing carboxylic acids and the derivatives thereof which can be used in this invention include the hydroxy-containing aromatic carboxylic acids, the anhydrides or a derivative thereof characterized, for example, by the formulae:

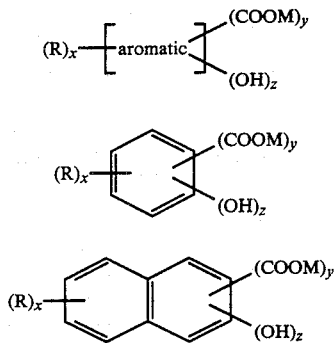

wherein R, in the above formula, is a substantially alkyl substituent, wherein at least one R group preferbly has at least 8, and, more preferably, at least an average of about 12 aliphatic carbon atoms; x is 1, 2 or 3; y is 1 or 2; z is 1, 2 or 3 and, M is selected from the group consisting of a metal, hydrogen, nitrogen and/or an alkyl group of 1 to 7 carbon atoms. Typically R has up to an average of 400 carbon atoms. In addition to the above, other saponifiable derivatives, e.g., amides, imides, halides, etc., capable of being overbased with magnesium or the magnesium compounds hereinafter described can be used in place of these acids.

The substituents on the carboxylic acid are preferably substantially hydrocarbyl, e.g., a substantially aliphatic hydrocarbyl, and these may contain small amounts of a non-hydrocarbyl group, e.g., polar groups. Either the aromatic ring and/or the alkyl substituent can be substituted with one or more polar groups, such as a halogen group, etc., in amounts ranging from about zero up to about 10% by weight without adversely affecting the desired characteristics of the basic carboxylic magnesium salts of this invention.

Of the various substituted aromatic hydroxy-containing carboxylic acids and the derivatives thereof included in the above formulae, the preferred hydroxy-containing substituted aromatic carboxylic acids include the ortho, meta and parahydroxy alkyl substituted aromatic carboxylic acids such as the alkyl-substituted hydroxy benzoic acids and, more preferably the alkyl-substituted salicylic acids and derivatives thereof. The substituted salicylic acids and the derivatives, for purposes of this invention, also include analogous acids derived from the fused ring hydrocarbons, e.g., naphthols and the like. As indicated, the alkyl substituents, i.e., the hydrocarbyl or substantially hydrocarbyl substituents and/or the aryl nucleus of the hydroxy-containing aromatic carboxylic acids, etc., can contain other substituents, including, for example, one or more polar groups selected from the class consisting of mercapto, halogen, nitro, amino, nitroso, sulfo, keto, oxo and various combinations thereof in amounts ranging up to about 10% by weight, i.e., from zero up to about 10% by weight of the composition. Specific examples of some of the various substituted aromatic hydroxy-containing carboxylic acids and the derivatives thereof, e.g., the $C_{16}$–$C_{32}$ alkyl-substituted hydroxy aromatic carboxylic acids include the mono- and polyhydroxy-containing alkyl-substituted aromatic carboxylic acids and the mono- and polycarboxylic hydroxy-containing alkyl-substituted aromatic carboxylic acids and the derivatives thereof such as, for example, the alkylated protocatechuic acids, e.g., an alkylated 3,4-dihydroxyaromatic carboxylic acid; an alkylated gallic acid, e.g., an alkyl-substituted 3,4,5-trihydroxyaromatic carboxylic acid; anacardic acid (o-pentadecadienyl salicylic acid); an alkylated gentisic acid, e.g., an alkyl-substituted 2,5-dihydroxy benzoic acid; an alkylated isophthalic acid, e.g., an alkyl-substituted 4-hydroxy-1,3-benzene dicarboxylic acid; an alkylated naphthoic acid, e.g., an alkyl-substituted 1-hydroxy-2-naphthoic acid or an alkyl-substituted 3-hydroxy-2-naphthoic acid; an alkylated 4,6-dihydroxy toluic acid, e.g., a $C_{16}$–$C_{24}$ alkyl-substituted ortho-orsellinic acid, etc.

Of the various substituted aromatic hydroxy-containing carboxylic acids and the derivatives thereof that can be used for purposes of this invention, a number of the preferred carboxylic acids and the derivatives thereof may be specifically illustrated and include, for example, the mono- and dialkali or alkaline earth metal salts of the ortho, meta or parahydroxy carboxylic substituted aromatic acids such as the alkyl-substituted monolithium salicylates, the alkyl-substituted sodium salicylates, monosodium-2-hydroxy-4-dialkyl benzoates, monolithium parahydroxy alkyl benzoates, lithium metahydroxy alkyl benzoates, the alkali metal salts of the alkyl-substituted hydroxy-containing phthalic acids or terephthalic acids, 2,4-dialkyl hydroxy benzoic acids octylsalicylic acid, pentadecenyl salicylic acid, octadecylsalicylic acid, octyl-4-hydroxybenzoic acid and combinations thereof.

The alkali and alkaline earth metal salts of the alkyl-substituted hydroxybenzoic acids wherein the alkyl substituents contain at least 16 aliphatic carbon atoms are particularly preferred and can include the salts of mixtures of the alkyl hydroxybenzoic acids, such as mixtures obtained by reacting, for example, salicylic acid or 4-hydroxybenzoic acid with a mixture of alkenes, e.g., a mixture of alkenes obtained by cracking a paraffinic hydrocarbon, etc. In addition, other metal salts include the mixtures obtained by alkylating phenols with one or more of a mixture of alkenes and subsequently converting the alkyl-substituted phenols to alkylsalicylic acids by the Kolbe-Schmidt reaction. As indicated, a particularly preferred class of substituted hydroxy-containing aromatic carboxylic acids include the alkyl-substituted salicylic acids and the derivatives thereof, e.g., metal salts, etc., and especially the salicylic acids wherein the alkyl groups are substantially long chain aliphatic, substantially hydrocarbon groups. These substituted salicylic acids, etc., can be derived, for example, from benzene or a phenol which has been alkylated with a hydrocarbon or substantially a hydrocarbon having at least about 8 aliphatic carbon atoms and preferably at least about 16 aliphatic carbon atoms, e.g., a substantially saturated aliphatic hydrocarbon. The alkyl or aliphatic hydrocarbon-substituted salicylic acids can include the individual acids, per se, and/or a mixture of said acids each having a different alkyl substituent including, for example, mixtures of alkyl-substituted salicylic acids having alkyl groups of from 8 to 18 aliphatic carbon atoms and alkyl groups of 16 to 32 carbon atoms, etc. The hydroxy-containing aromatic carboxylic acids can be substituted with one or more alkyl groups, e.g., substantially aliphatic hydrocarbon groups preferably having at least 8 carbon atoms and up to about 10,000 aliphatic carbon atoms. Generally, however, the hydrocarbon or substantially aliphatic hydrocarbon substituents can have average molecular weights ranging from about 100 up to about 100,000 or higher and preferably from about 200 to about 10,000. For example, the hydrocarbon or substantially aliphatic hydrocarbon substituents may be derived by polymerization of a lower molecular weight olefin, e.g., a monoolefin, having from 2 to 30 carbon atoms per molecule. A particularly preferred class of such hydrocarbon substituents are derived from polymers of the lower monoolefins such as polyethylene, polypropylene, polyisobutylene and copolymers of ethylene and propylene having average molecular weights ranging from about 100 to about 10,000 and preferably from about 300 to 700. More specifically, polymers, i.e., copolymers, terpolymers, etc. which may be used in preparing the alkyl or hydrocarbon substituted hydroxy-containing aromatic carboxylic acids include polymers of the monoolefins such as ethylene, propylene, 1-butene, 1-isobutene, 1-hexene, 1-octene, 2-methyl-1-heptene, 3-cyclohexyl-1-butene, 2-methyl-5-propyl-1-hexene, etc.

In addition, polymers of olefins wherein the olefinic linkage is not in the terminal position are likewise useful and can include, for example, polymers of 2-butene, 3-pentene, 4-octene, etc. Further interpolymers of the monoolefins that can be used include, for example, polymers of the monoolefins illustrated above with other interpolymerizable olefinic compounds such as the aromatic olefins, cyclic olefins, polyolefins, etc. More specifically, the interpolymers can be prepared, for example, by polymerizing isobutene with styrene; isobutene with butadiene; propene with isoprene; ethylene with propylene; ethylene with piperylene; isobutene with chloroprene; diisobutene with p-methylstyrene; 1-hexene with 1,3-hexadiene; 1-octene with 1-hexene; 1-heptene with 1-pentene; 3-methyl-1-butene with 1-octene; 3,3-dimethyl-1-pentene with 1-hexene; isobutene with styrene and piperylene, etc.

The relative proportions of the monoolefin and the other monomers used in preparing the polymers influence the stability and oil-solubility of the carboxylic magnesium salts of this invention and therefore said polymers should be substantially aliphatic and preferably substantially saturated, aliphatic hydrocarbon polymers. More particularly, for purposes of this invention, it is preferred that the polymers contain at least about 95% by weight of saturated units derived from aliphatic monoolefins and no more than about 5% by weight of the olefinic linkages based on the total carbon-to-carbon covalent linkages in the hydrocarbon substituent. In a more preferred embodiment, the percent of olefinic linkages should be less than about 2% by weight of the total carbon-to-carbon covalent linkages in said substantially aliphatic hydrocarbon. Moreover, if an aryl substituted olefin is employed, e.g., styrene, etc., the amounts should be limited to provide no more than up to about 10% by weight of the aryl substituent, e.g., 0 to about 10% by weight.

Specific examples of the polymers include, for example, a copolymer of 95% by weight of isobutene with 5% by weight of styrene; a terpolymer of 98% by weight of isobutene with 1% by weight of piperylene and 1% by weight of chloroprene; a terpolymer of 95% by weight of isobutene with 2% by weight of 1-butene and 3% by weight of 1-hexene; a terpolymer of 60% by weight of isobutene with 20% by weight of 1-pentene and 20% by weight of 1-octene; a copolymer of 80% by weight of 1-hexene and 20% by weight of 1-heptene; a terpolymer of 90% by weight of isobutene with 2% by weight of cyclohexene and 8% by weight of propene; a copolymer of 80% by weight of ethylene and 20% by weight of propene; etc. In addition, other hydrocarbon substitutents include the substituted aliphatic hydrocarbons, e.g., obtained by halogenating polyisobutylene, polypropylene, polyethylene and copolymers of ethylene and propylene, etc., which may have average molecular weights ranging from about 300 to 10,000 and preferably from about 700 to 5000.

As indicated, the oil soluble basic metal salts, e.g., magnesium salts of this invention can be obtained by reacting either a substituted aromatic hydroxy-containing carboxylic acid or a saponifiable derivative of said acid, e.g., a metal salt with a stoichiometric excess of a basically magnesium compound in the presence of at least about 0.1 mole of water for each equivalent of said magnesium compound and then refluxing the resulting reaction mixture until it is substantially haze-free.

The substituted aromatic hydroxy-containing carboxylic acid substantially neutral metal salt to be subsequently overbased with the magnesium oxide can be obtained by reacting the substituted hydroxy-containing carboxylic acid or a derivative thereof, i.e., the anhydride, halide, ester, etc., with one or more metals or metal compounds and particularly with a metal or metal compound wherein the metal is selected from the class consisting of the alkali and alkaline earth metals of Groups I and II of the Periodic Table.

Other metals or metal compounds which can be used either alone or in combination to prepare the carboxylic metal salt intermediates include, for example, aluminum, tin, cobalt, nickel, etc. Specific examples of the metal compounds include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin butylate, cobalt oxide, cobalt hydroxide, cobalt carbonate, cobalt pentylate, nickel oxide, nickel hydroxide, nickel carbonate, mixtures thereof, etc. The carboxylic metal salts for purposes of this invention can be classified as acidic salts, neutral salts or basic salts. The term "acidic salts" includes, for example, a dicarboxylic acid wherein only one of the two carboxylic-acid groups is converted to the salt leaving a free carboxylic-acid group in its molecular structure. The term "neutral salt" includes a dicarboxylic acid, for example, wherein both of the carboxylic-acid groups are converted to salt groups. These neutral salts may be prepared from the reaction of one chemical equivalent of a dicarboxylic acid with one chemical equivalent of a metal or metal compound. In some instances, more than the calculated stoichiometric amount of metal may be incorporated into the carboxylic acid to form the basic salt. The "basic salt", therefore, includes a metal salt wherein the metal is present in a calculated stoichiometric amount greater than the acid radical. Thus, the basic metal salts of the aromatic hydroxy-containing carboxylic acids may be characterized as metal salts wherein the chemical equivalents of metal e.g., magnesium are in excess of the total chemical equivalents of acid groups. Accordingly, for purposes of this invention, the ratio between the total equivalents of metal, e.g., magnesium to equivalents of acid is greater than 1.0 and may range up to about 15 chemical equivalents of metal for each chemical equivalent of acid, e.g., for each calculated chemical equivalent of a hydrocarbon-substituted salicylic acid.

A "basic salt" therefore is a metal salt, e.g., a basic magnesium salt wherein the magnesium is present in a stoichiometrically greater amount than the organic acid radicals. These basic metal salts may be characterized as having a metal ratio greater than 1.0. The term "metal ratio" is the ratio of the total chemical equivalents of metal in the salt to the chemical equivalents of organic acid groups present. Thus, the metal ratio may be characterized as a measure of the calculated stoichiometric excess of a metal in a particular metal salt of one or more organic acids. This term and its use is well known in the art as particularly pointed out, for example, in U.S. Pat. No. 3,271,310, the disclosure of which is hereby incorporated by reference. In addition to the substituted aromatic hydroxy-containing carboxylic metal salt derivatives, e.g., substituted salicylic metal salts, other derivatives including the anhydrides, halides, and lower alkyl esters, e.g., esters derived from lower aliphatic alcohols having 1.0 to 8 carbon atoms, can be used to prepare the basic carboxylic magnesium salts of this invention.

For purposes of this invention, magnesium is considered as an alkaline earth metal and as having two chemical equivalents per atomic weight. Similarly, basically reactive magnesium compounds such as magnesium oxide or magnesium hydroxide, etc., have two chemical equivalents per molecule. Basically reactive magnesium compounds are those components that react with a carboxylic acid, salt or saponifiable derivative thereof to form an overbased magnesium salt. Among the basically reactive magnesium compounds useful in the present invention are lightly calcined magnesium oxide, freshly prepared magnesium hydroxides and magnesium alcoholates which have been stored out of contact with carbon dioxide. The amount of basically magnesium compound to be employed for purposes of preparing the basic magnesium carboxylic salts must be at least a stoichiometric excess, i.e., an excess over that amount of magnesium normally required to obtain neutral salts of the total acid present and may range up to about 15 chemical equivalents of magnesium, e.g., derived from magnesium oxide, for each chemical equivalent of the substituted aromatic hydroxy-containing carboxylic acid or a derivative thereof. Preferably, an excess of about 0.5 to about 5.0 equivalents can be used. Among the basically reactive magnesium compounds which can be used to overbase the substituted hydroxy-containing carboxylic acid or its derivatives are the commercially available magnesium oxides in lightly or actively calcined form. The lightly calcined form of magnesium oxide is preferred and is available from various sources under Trade Names such as Morton Elastomag 20, Elastomag 100, Elastomag 170, Dow Synthetic Magnesite, Dow Tectum, etc.

In reacting the magnesium compound with the substituted aromatic hydroxy-containing carboxylic acids or a derivative thereof, at least about 0.1 mole of water must be present for each chemical equivalent of said magnesium oxide. Preferably, however, from about 0.1 mole up to about 10 moles of water or more are present for each chemical equivalent of magnesium oxide. Generally, however, the ratio of water to magnesium oxide will range from about 0.1 to 5.0 and 0.1 to 2.0 moles of water for each chemical equivalent of magnesium oxide present in the reaction.

In preparing the basic metal carboxylic salts, e.g., overbased magnesium carboxylic salts of this invention, the substituted aromatic hydroxy-containing carboxylic acid or a derivative thereof is reacted with the magnesium oxide in the presence of an effective amount of water. Optionally the reaction is carried out in the presence of at least one sulfur-containing organic acid. Usually about 0.05 to about 0.25 equivalent of such acid is used. Derivatives of sulfur-containing acid, e.g., anhydrides, salts, halides, esters, etc., can also be used. These acids and the derivatives are used, if they are present, in amounts ranging up to about 0.25 chemical equivalent of said sulfur-containing organic acid or its derivative for each chemical equivalent of the above-identified substituted aromatic hydroxy-containing carboxylic acid or its derivative. Preferably, the sulfur-containing organic acid or its derivative is present in an amount ranging from about 0.05 to about 0.25 and, more preferably, in an amount ranging from about 0.05 to about 0.1 chemical equivalent of said organic acid or its derivatives for each chemical equivalent of said substituted aromatic hydroxy-containing carboxylic acid or its derivative.

The sulfur-containing organic acids and the derivatives that are particularly useful include the acids or acid-producing compounds, i.e., derivatives of organic acids, which are susceptible to being overbased with a metal, e.g., magnesium. These acids are typically sulfonic acids, and the derivatives thereof, including the metal salts, the halides, anhydrides and esters derived from the lower aliphatic alcohols having up to 8 carbon atoms.

The sulfur-containing organic acids which can be used in this invention include the sulfonic acids, sulfamic acids, sulfinic acids, thiosulfonic acids and the various derivatives thereof. Of these, the sulfonic acids and the derivatives thereof are particularly useful and include the aliphatic-substituted sulfonic acids wherein the aliphatic substituent or substituents contain at least 8 carbon atoms. These sulfonic acids include the alkylarylsulfonic acids, alkylalicyclic sulfonic acids, alkylheterocyclic sulfonic acids and aliphatic sulfonic acids wherein the aliphatic radicals contain at least 12 aliphatic carbon atoms. Specific examples of sulfonic acids and the derivatives thereof include the petroleum sulfonic acids, mono- and polywax-substituted naphthylene sulfonic acids, phenolsulfonic acids, diphenylethersulfonic acids, diphenyletherdisulfonic acids, naphthylenedisulfide sulfonic acids, naphthylenedisulfide disulfonic acids, diphenylamine disulfonic acids, diphenylamine sulfonic acids, thiophene sulfonic acids, chloronaphthylene sulfonic acids, etc. Other substituted sulfonic acids include the cetylchlorobenzene sulfonic acids, cetylphenolsulfonic acids, cetylphenoldisulfide sulfonic acids, cetylphenolmonosulfide sulfonic acids, dilaurylbetanaphtholsulfonic acids, dicaprylnitronaphthylene sulfonic acids, the aliphatic sulfonic acids such as the paraffin wax sulfonic acids, the unsaturated paraffin wax sulfonic acids, the hydroxy-substituted paraffin wax sulfonic acids, tetraisobutylene sulfonic acid, tetraamyl sulfonic acid, chloro-substituted paraffin wax sulfonic acids, nitroso-paraffin wax sulfonic acids, petroleum naphthylene sulfonic acids, the polywax-substituted cycloalkylsulfonic acids and various derivatives of these acids particularly the alkali and alkaline earth metal salts of these acids. The petroleum sulfonic acids include a well-known class of sulfonic acids derived from petroleum products as particularly disclosed, for example, in U.S. Pat. Nos. 2,480,638; 2,483,800; 2,718,265; 2,726,261; 2,794,829; 2,832,801; 3,225,086; 3,337,613; 3,351,655; 2,616,904; 2,616,905; 2,723,235; 2,723,236 and 2,777,874.

An important feature of this invention is that the alkyl substituted aromatic hydroxy-containing carboxylic acid, e.g., alkyl substituted salicylic acid, etc., can be overbased with magnesium oxide in the presence of water without relying on the use of a promoter, e.g., alcohol, phenol, etc., and an inorganic acidic material, e.g., carbon dioxide, etc., as required heretofore. In the present invention, the aromatic hydroxy-containing carboxylic acid or a derivative thereof is reacted with a stoichiometric excess of basically reactive magnesium compound, e.g., excess of about 0.1 to about 15 equivalents, in the presence of water and optionally in the presence of up to about 0.25 chemical equivalents of at least one other sulfur-containing organic acid, e.g., a sulfonic acid, or a derivative thereof at a temperature of at least about 25° C. Preferably, the temperatures range from about 80° C. up to about 300° C. and still more preferably the temperatures range from about 80° C. to 200° C. or 100° C. to 175° C.

The reaction is carried out, preferably, in the presence of at least one substantially inert organic liquid which may range up to about 80% by weight of the total composition and preferably from about 10% to 50% by weight of the composition. These organic liquids include various commercially available solvents and particularly mineral oils including, for example, Stoddard Solvent, the aliphatic, alicyclic and aromatic hydrocarbons, substituted hydrocarbons and the corresponding halogenated hydrocarbons such as chlorobenzene, etc., and various combinations thereof. The inert organic liquid can be an oil soluble fluid preferably comprising mineral oil and at least one other diluent soluble in said mineral oil but substantially less viscous than the oil. These diluents may include, for example, a combination of mineral oil with one or more aliphatic, alicyclic or aromatic hydrocarbons and halogenated hydrocarbons including, for example, kerosene, xylene, toluene, ethylbenzene, propylbenzene, cumene, fluorobenzene, chlorobenzene, bromobenzene, fluorotoluene, heptene, octene, nonane, decane, trimethylpentane, cyclohexane, cycloheptane, ethylcyclohexane, cyclooctane and various combinations of these.

In preparing the carboxylic metal salts of this invention, the process comprises contacting and reacting, in any order, one or more of the reactants at about room temperature and higher. Thus, for example, the acids or the derivatives thereof may be contacted and reacted with the magnesium compound in the presence of effective amounts of water and an organic diluent at temperatures ranging up to about 300° C. or higher. The maximum temperature is obviously the decomposition temperature of the reaction mass or any one of the individual reactants or products and is preferably between about 175° C. and about 200° C.

After the above-recited components are reacted the reaction mixture is refluxed for at least about 0.5 hour. Usually the reaction is refluxed until it is haze-free. A mixture is considered haze-free when no haze appears upon inspection by the naked eye against daylight. Normally this reflux period is between 0.5 to 5.0, usually 0.5 to 2.5 hours.

As indicated, the hydroxy-containing carboxylic overbased metal salts of this invention can be obtained by various processes and preferably by utilizing a hydroxy-containing carboxylic acid, anhydride or metal salt thereof, e.g., a magnesium salt of an alkylated salicylate and subsequently adding a stoichiometric excess of the magnesium compound to obtain a carboxylic composition wherein the metal ratio range is in excess of 1.0 and up to about 15. Thus, for example, various metal salts of the substituted aromatic hydroxy-containing carboxylic acid, e.g., the alkali or alkaline earth metal salt may be prepared, initially, and used as an intermediate in the subsequent overbasing of said carboxylic salts with magnesium oxide to obtain the basic metal salts. While the primary purpose of this invention is to provide an overbased or basic magnesium salt of a hydroxy-containing aromatic carboxylic acid, it is obvious that it is not necessary to have only magnesium as the metal present in the carboxylic composition. In fact, other metals selected from Groups I and II of the Periodic Table may be present in the basic carboxylic magnesium salts. For example, if an alkali or alkaline earth metal salt other than the magnesium salt is employed, initially, as the starting material, the basic magnesium salt will include that metal which was present in the starting material. When a metal salt, for example, is used as an intermediate, e.g., an alkali metal salt of an alkylated salicyclic acid, the salt may be either an acidic, neutral or basic salt, e.g., having a strochiometric excess of one or more metals. Either the acidic, neutral or basic metal salts of the aromatic hydroxy-containing carboxylic acids may be reacted with a stoichiometric excess of magnesium oxide to obtain a product having a metal ratio ranging up to about 15. As stated above, the products of this inventive process have magnesium content of at least about 150%, preferably about 200%, most preferably about 250% of the stoichiometrically equivalent amount, based on the total equivalents of acid present. For example, if there were 0.9 equivalents of hydroxy aromatic acid and 0.1 equivalent of sulfonic acid present according to this invention the product of this invention would contain at least 1.5, preferably 2.0, most preferably 2.5 equivalents of magnesium present.

In the following examples which illustrate the process and products of this invention, all parts and percentages are parts and percentages by weight unless stated to the contrary and the magnesium oxide is lightly calcined magnesium oxide unless otherwise noted.

EXAMPLE 1

A reaction mixture comprising about 512 parts by weight of a mineral oil solution containing about 0.5 equivalent of a substantially neutral magnesium salt of an alkylated salicyclic acid wherein the alkyl group has an average of about 18 aliphatic carbon atoms and about 30 parts by weight of an oil mixture containing about 0.037 equivalent of an alkylated benzenesulfonic acid together with about 15 parts by weight (about 0.65 equivalent) of a magnesium oxide and about 250 parts by weight of xylene is added to a flask and heated to a temperature of about 60° C. to 70° C. The reaction mass is subsequently heated to about 85° C. and approximately 60 parts by weight of water are added. The reaction mass is held at a reflux temperature of about 95° C. to 100° C. for about 1½ hours and subsequently stripped at a temperature of 155° C.–160° C., under a vacuum, and filtered. The filtrate comprises the basic carboxylic magnesium salt characterized by a sulfated ash content of 12.35% (ASTM D-874, IP 163), indicating that the salt contains 200% of the stoichiometrically equivalent amount of magnesium.

EXAMPLE 2

A reaction mixture comprising about 506 parts by weight of a mineral oil solution containing about 0.5 equivalent of a substantially neutral magnesium salt of an alkylated salicylic acid wherein the alkyl groups have an average of about 16 to 24 aliphatic carbon atoms and about 30 parts by weight of an oil mixture containing about 0.037 equivalent of an alkylated benzenesulfonic acid together with about 22 parts by weight (about 1.0 equivalent) of a magnesium oxide and about 250 parts by weight of xylene is added to a flask and heated to temperatures of about 60° C. to 70° C. The reaction is subsequently heated to about 85° C. and approximately 60 parts by weight of water are added to the reaction mass which is then heated to the reflux temperature. The reaction mass is held at the reflux temperature of about 95°–100° C. for about 1½ hours and subsequently stripped at about 155° C., under 40 mm Hg, and filtered. The filtrate comprises the basic carboxylic magnesium salts and is characterized by a sulfated ash content of 15.59% (sulfated ash) corresponding to 274% of the stoichiometrically equivalent amount.

EXAMPLE 3

A reaction mixture comprising about 4048 parts by weight of a mineral oil solution containing about 4.0 equivalents of a substantially neutral magnesium salt of an alkylated salicylic acid wherein the alkyl groups have an average of 16 to 24 aliphatic carbon atoms and about 240 parts by weight of an oil mixture containing about 0.3 equivalent of an alkylated benzenesulfonic acid together with about 176 parts by weight (about 8.0 equivalents) of a magnesium oxide and approximately about 2000 parts by weight of xylene is added to a flask and heated to temperatures of about 60°–75° C. The reaction mass is subsequently heated to about 82° C., and approximately 480 parts by weight of water are added to the reaction which is then heated to the reflux temperature. The reaction mass is held at reflux temperature of about 95°–100° C. for about 1 hour and subsequently stripped at a temperature of about 170° C., while blowing with nitrogen, and then further stripped at 155° C., under 40 mm Hg, and filtered. The filtrate comprises the basic carboxylic magnesium salts and has a sulfated ash content of 15.77% (sulfated ash) corresponding to 277% of the stoichiometrically equivalent amount.

EXAMPLE 4

A substantially neutral magnesium salt of an alkylated salicylic acid wherein the alkyl groups have from 16 to 24 aliphatic carbon atoms is prepared by reacting approximately stoichiometric amounts of magnesium chloride with a substantially neutral potassium salt of said alkylated salicylic acid. A reaction mass comprising approximately 6580 parts by weight of a mineral oil solution containing about 6.50 equivalents of said substantially neutral magnesium salt of the alkylated salicylic acid and about 388 parts by weight of an oil mixture containing about 0.48 equivalent of an alkylated benzenesulfonic acid together with approximately 285 parts by weight (14 equivalents) of a magnesium oxide and approximately 3252 parts by weight of xylene is added to a flask and heated to temperatures of about 55° C. to 75° C. The reaction mass is then heated to about 82° C. and approximately 780 parts by weight of water are added to the reaction which is subsequently heated to the reflux temperature. The reaction mass is held at the reflux temperature of about 95°–100° C. for about 1 hour and subsequently stripped at a temperature of about 170° C., under 50 mm Hg, and filtered. The filtrate comprises the basic carboxylic magnesium salts and has a sulfated ash content of 15.7% (sulfated ash) corresponding to 276% of the stoichiometrically equivalent amount.

EXAMPLE 5

A reaction mixture comprising approximately 1025 parts by weight of a mineral oil solution containing about 1.0 equivalent of a substantially neutral magnesium salt of an alkylated salicylic acid wherein the alkyl groups have an average of about 18 aliphatic carbon atoms and about 60 parts by weight of an oil mixture containing an alkylated benzenesulfonic acid (0.04 equivalent) and about 0.04 equivalent of oleic acid together with about 60 parts by weight (3.0 equivalents) of a magnesium oxide and about 500 parts by weight of xylene is added to a flask and heated to temperatures of about 65° C. to 75° C. The reaction mass is subsequently heated to about 90° C. and approximately 240 parts by weight of water are added to the flask which is then heated to the reflux temperature. The reaction mass is held at the reflux temperature of about 95° C.–100° C. for about 2 hours and subsequently stripped at a temperature of about 160° C. and filtered. The filtrate comprises the basic carboxylic magnesium salts.

EXAMPLE 6

A reaction mixture comprising approximately 1500 parts by weight of a mineral oil solution containing about 1.5 equivalents of a substantially neutral magnesium salt of an alkylated salicylic acid wherein the alkyl groups have an average of about 16 to 24 aliphatic carbon atoms and about 90 parts by weight of an oil mixture containing an alkylated benzenesulfonic acid (0.08 equivalent) and about 0.04 equivalent of a tall oil fatty acid, together with about 60 parts by weight (3.0 equivalents) of a magnesium oxide and about 500 parts by weight of xylene is added to a flask and heated to a temperature of about 65° C. The reaction mass is then heated to about 85° C. and approximately 180 parts by weight of water are added to the reaction which is then heated to the reflux temperature. The reaction mass is held at the reflux temperature of about 95° C.–100° C. for about 2 hours and subsequently stripped at a temperature of about 155° C., under 40 mm Hg, and filtered. The filtrate comprises the basic carboxylic magnesium salts.

EXAMPLE 7

A reaction mixture comprising approximately 1025 parts by weight of a mineral oil solution containing about 1.0 equivalent of a substantially neutral magnesium salt of an alkylated salicylic acid wherein the alkyl group has an average of at least about 18 aliphatic carbon atoms and about 0.08 equivalent of a petroleum naphthenesulfonic acid together with approximately 60 parts by weight (3.0 equivalents) of a magnesium oxide and about 750 parts by weight of xylene is added to a flask and heated to a temperature of about 75° C. The reaction mass is subsequently heated to about 85° C. and approximately 440 parts by weight of water are added to the reaction which is then heated to the reflux temperature. The reaction mass is held at the reflux temperature of about 95° C.–100° C. for about 2 hours and subsequently stripped at a temperature of about 160° C., under 40 mm Hg, and filtered. The filtrate comprises the basic carboxylic magnesium salts.

EXAMPLE 8

A reaction mixture comprising approximately 1025 parts by weight of an oil solution containing about 1.0 equivalent of an alkylated hydroxybenzoic acid wherein the alkyl group has an average of about 18 aliphatic carbon atoms and an oil mixture containing about 0.08 equivalent of a sodium salt of an alkylated benzenesulfonic acid together with about 60 parts by weight (3.0 equivalents) of a magnesium oxide and about 500 parts by weight of a solvent containing xylene is added to a flask and heated to temperatures ranging from about 60°–75° C. The reaction mass is subsequently heated to about 85° C., and approximately 60 parts by weight of water are added to the mass which is then heated to the reflux temperature. The reaction mass is held at the reflux temperature of about 95° C.–100° C. for about 2 hours and subsequently stripped at a temperature of about 150° C., under 40 mm Hg, and filtered. The filtrate comprises the basic carboxylic metal salts.

EXAMPLE 9

A reaction mixture comprising approximately 512 parts by weight of an oil solution containing about 0.5 equivalent of a substantially neutral sodium salt of an alkylated salicylic acid wherein the alkyl groups have an average of about 16 to 24 aliphatic carbon atoms and an oil mixture containing approximately 0.25 equivalent of an alkylated benzenesulfonic acid together with about 4.0 equivalents of a magnesium oxide and about 5000 parts by weight of xylene is added to a flask and heated to a temperature of about 75° C. The reaction is subsequently heated to about 85° C. and approximately 200 parts by weight of water are added to the reaction mass which is then heated to the reflux temperature. The reaction mass is held at the reflux temperature of about 95° C. to 100° C. for about 2 hours and subsequently stripped at a temperature of about 150° C., under a vacuum, and filtered. The filtrate comprises the basic carboxylic magnesium salts.

EXAMPLE 10

A reaction mixture comprising approximately 1025 parts by weight of a mineral oil solution containing about 1.0 equivalent of a substantially neutral calcium salt of an alkylated salicylic acid wherein the alkyl groups have an average of about 16 to 24 aliphatic carbon atoms and an oil mixture containing about 0.12 equivalent of a sodium salt of an alkylated benzenesulfonic acid together with about 60 parts by weight (3.0 equivalents) of a magnesium oxide and about 750 parts by weight of an organic solvent containing xylene is added to a flask and heated to temperatures ranging from about 60°–70° C. The reaction mass is subsequently heated to about 85° C. and approximately 200 parts by weight of water are added to the reaction which is then heated to the reflux temperature. The reaction mass is held at the reflux temperature of about 95° C. to 100° C. for about 2 hours and subsequently stripped under a vacuum, at a temperature of about 165° C. The filtrate comprises the basic carboxylic magnesium salts.

EXAMPLE 11

A reaction mixture comprising approximately 512 parts by weight of a mineral oil solution containing about 0.5 equivalent of a substantially neutral magnesium salt of an alkylated hydroxybenzoic acid wherein the alkyl groups have an average of at least 18 aliphatic carbon atoms and an oil mixture containing about 0.04 equivalent of a naphthenic acid together with about 60 parts by weight (3.0 equivalents) of a magnesium oxide and about 500 parts by weight of xylene is added to a flask and heated to temperatures ranging from about 60°–70° C. The reaction mass is subsequently heated to about 85° C. and approximately 180 parts by weight of water is added to the reaction which is subsequently heated to the reflux temperature. The reaction mass is held at the reflux temperature of about 95° C. to 100° C. for about 2 hours and subsequently stripped, under vacuum, at a temperature of about 150° C. and filtered. The filtrate comprises the basic carboxylic magnesium salts.

EXAMPLE 12

A reaction mixture comprising approximately 1025 parts by weight of an oil solution containing about 1.0 equivalent of an alkylated gallic acid wherein the alkyl group has an average of about 18 aliphatic carbon atoms and an oil mixture containing about 0.1 equivalent of a sodium salt of a petroleum sulfonic acid together with about 60 parts by weight (3.0 equivalents) of a magnesium oxide and about 500 parts by weight of an organic solvent containing xylene is added to a flask and heated to temperatures ranging from about 60° C.–75° C. The reaction mass is subsequently heated to about 85° C. and approximately 120 parts by weight of water are added to the reaction which is then heated to the reflux temperature. The reaction mass is held at the reflux temperature of about 95°–100° C. for about 2 hours and subsequently stripped at a temperature of about 160° C., under vacuum, and filtered. The filtrate comprises the basic carboxylic magnesium salts.

EXAMPLE 13

A reaction mixture comprising approximately 1000 parts by weight of an oil solution containing about 1.0 equivalent of an alkylated 2,5-dihydroxybenzoic acid wherein the alkyl group has an average of about 16 aliphatic carbon atoms and an oil mixture containing about 0.05 equivalent of a petroleum sulfonic acid and about 0.05 equivalent of a tall oil fatty acid together with about 160 parts by weight (8.0 equivalents) of a magnesium oxide and about 600 parts by weight of an organic solvent containing xylene is added to a flask and heated to temperatures ranging up to about 60°–75° C. The reaction mass is subsequently heated to about 85° C. and approximately 90 parts by weight of water are added to the reaction which is then heated to the reflux temperature. The reaction mass is held at the reflux temperature of about 95°–100° C. for about 3 hours and subsequently stripped at a temperature of about 150° C., under a vacuum, and filtered. The filtrate comprises the basic carboxylic magnesium salts.

EXAMPLE 14

A reaction mixture comprising approximately 1575 parts by weight of an oil solution containing about 1.5 equivalents of an alkylated 4-hydroxy-1,3-benzenedicarboxylic acid wherein the alkyl group has an average of at least about 16 aliphatic carbon atoms and an oil mixture containing about 0.5 equivalent of a tall oil fatty acid together with about 120 parts by weight (6.0 equivalents) of a magnesium oxide and about 700 parts by weight of an organic solvent containing xylene is added to a flask and heated to temperatures ranging from about 70°–75° C. The reaction is subsequently heated to about 85° C. and approximately 200 parts by weight of water are added to the reaction which is then heated to the reflux temperature. The reaction mass is held at the reflux temperature of about 95°–100° C. for about 3 hours and subsequently stripped at a temperature of about 155° C., under vacuum, and filtered. The filtrate comprises the basic carboxylic magnesium salts.

EXAMPLE 15

A reaction mixture comprising approximately 500 parts by weight of an oil solution containing about 0.5 equivalent of an alkylated 1-hydroxy-2-naphthoic acid wherein the alkyl group has an average of at least about 16 aliphatic carbon atoms and an oil mixture containing 0.25 equivalent of a petroleum sulfonic acid together with about 30 parts by weight (1.5 equivalents) of a magnesium oxide and about 250 parts by weight of an organic solvent is added to a reactor and heated to temperatures ranging to about 60°–75° C. The reaction mass is subsequently heated to about 85° C. and approximately 30 parts by weight of water are added to the mass which is then heated to the reflux temperature. The reaction mass is held at the reflux temperature of about 95°–100° C. for about 2 hours and subsequently stripped at a temperature of about 150° C., under vacuum, and filtered. The filtrate comprises the basic carboxylic magnesium metal salts.

EXAMPLE 16

(a) To 6240 grams of a potassium salt of a $C_{16-24}$ substituted salicyclic acid in a mineral oil diluent is added, over a period of one hour, 309 grams of sulfur dichloride. The reaction mixture is held at 150° C. during the addition. After the addition, the reaction is cooled to 120° C., and 700 grams of xylene and 300 grams of water are added to it. The mixture is refluxed for 0.75 hour and then stripped to a temperature of 165° C. while nitrogen is bubbled through it. Filtration through filter aid provides the desired diaryl sulfide intermediate.

(b) To a mixture of 509 grams of the diaryl sulfide described in (a), 250 grams of xylene, 34 grams of the sulfonic acid described in Example 1, is added 33 grams of lightly calcined magnesium oxide. The reaction temperature is held at 60° C. during the addition. The temperature is then raised to 85° C. and 60 grams of water is added to it. The reaction mixture is refluxed at 95° C. for 1.0 hour, stripped to 180° C. at 30 mm Hg and filtered through filter aid to provide the final product. This product has a magnesium sulfate content of 15.76% indicating that it contains 270% of the stoichiometrically equivalent amount of magnesium.

EXAMPLE 17

A reaction charge composed of 256 parts of the mineral oil solution described in Example 1 and an oil mixture containing about 0.019 parts of the sulfonic acid described in Example 1 is added to a flask. To this mixture is added a suspension containing 22 parts of freshly precipitated magnesium hydroxide formed by treating an aqueous solution containing 36 parts of magnesium chloride with 3.75 liters of 1 normal sodium hydroxide. One hundred twenty-five (125) parts of xylene is also added to the reactor and its contents are heated to about 60° C. to 70° C. The reaction mixture is subsequently treated with about 60 parts of water and held at reflux (95° C. to 105° C.) for 1.5 hours. The desired product is obtained by stripping the reaction mixture with nitrogen blowing at 155° C. to 160° C. at a pressure of 30 mm Hg and filtering the residue.

EXAMPLE 18

A reaction mixture comprising about 512 parts by weight of a mineral oil solution containing about 0.5 equivalent of a substantially neutral magnesium salt of an alkylated salicylic acid wherein the alkyl groups have an average of about 16 to 24 aliphatic carbon atoms with about 15 parts by weight (0.75 equivalent) of a magnesium oxide and about 250 parts by weight of xylene are added to a reactor at temperatures of about 60° C. to 70° C. The reaction mass is subsequently heated to about 85° C. and approximately 60 parts by weight of water are added to the reaction which is heated to reflux temperatures. The reaction mass is held at reflux temperatures of about 95° C. to 100° C. for 1½ hours and subsequently stripped at about 155° C., under 40 mm Hg, and filtered. The filtrate comprises the basic carboxylic magnesium salt.

EXAMPLE 19

A reaction mixture comprising about 472 parts by weight of a mineral oil solution containing about 0.333 equivalent of a substantially neutral magnesium salt of an alkylated salicylic acid wherein the alkyl groups have an average of about 60 aliphatic carbon atoms and about 26 parts by weight of an oil mixture containing about 0.333 equivalent of an alkylated benzenesulfonic acid together with about 15 parts by weight (about 0.69 equivalent) of a magnesium oxide and about 340 parts by weight of xylene is added to a flask and heated to temperatures of about 60° C. to 70° C. The reaction is subsequently heated to about 85° C. and approximately 65 parts by weight of water are added to the reaction mass which is then heated to the reflux temperature. The reaction mass is held at the reflux temperature of about 95°–100° C. for about 1 hour. An additional charge of 18 parts by weight (about 0.83 equivalent) of MgO is added to the reaction mass. The reaction mass is held at the reflux temperature of about 95°–100° C. for about 2 hours, then stripped to 200° C., under 18 mm Hg, and filtered. The filtrate is a mineral oil solution of the desired product.

EXAMPLE 20

A reaction mixture comprising about 2921 parts by weight of a mineral oil solution containing about 2.0 equivalents of a substantially neutral magnesium salt of an alkylated salicylic acid wherein the alkyl groups have an average of about 60 aliphatic carbon atoms and about 121 parts by weight of an oil mixture containing about 0.15 equivalent of an alkylated benzenesulfonic acid together with about 89 parts by weight (about 4.1 equivalents) of a magnesium oxide and about 2060 parts by weight of xylene is added to a flask and heated to temperatures of about 60° C. to 70° C. The reaction is subsequently heated to about 85° C. and approximately 540 parts by weight of water is added to the reaction mass which is then heated to the reflux temperature. The reaction mass is held at the reflux temperature of about 95°–100° C. for about 1½ hours and subsequently stripped at about 155° C., under 40 mm Hg, and filtered. The filtrate comprises the basic carboxylic magnesium salts and is characterized by a sulfated ash content of 8.18% (sulfated ash) corresponding to 228% of the stoichiometrically equivalent amount.

The carboxylic metal salts of this invention can be effectively employed in a variety of lubricating and fuel compositions. The lubricating compositions include primarily crankcase lubricating oils for spark-ignited and compression-ignited internal combustion engines including automobile and truck engines, two-cycle engine lubricants, aviation piston engines, marine and railroad diesel engines and the like. In addition, however, automotive transmissions, trans-axle lubricants, gear lubricants, metal-working lubricants, hydraulic fluids and various other lubricating oils and greases can be improved by the incorporation therein of a small but effective amount of the carboxylic compositions of this invention.

More specifically, the substituted aromatic hydroxy-containing carboxylic compositions, e.g., particularly the overbased magnesium salts of the alkylated benzoic acids such as the alkylated salicylic acids as described hereinabove, may be employed in effective amounts as an additive, e.g., as a dispersant having oxidation-inhibiting properties in amounts ranging up to about 30% by weight of the composition. More specifically, these substituted aromatic hydroxy-containing basic magnesium salts may be used in various oleaginous materials, including, for example, the synthetic and mineral lubricating oils, the normally liquid fuels, e.g., gasoline, diesel fuel, kerosene, etc., in amounts ranging from about 0.0001% up to about 25% or 30% by weight of the total composition. Preferably, however, the basic magnesium carboxylic salts are used in amounts ranging from about 0.01% to 30% by weight and more preferably in amounts ranging from about 0.1% to 10% by weight of the total composition. The optimum amount added to a particular oleaginous material will depend upon the particular type of surface or conditions to which the fuel or lubricant is to be subjected. For example, if the overbased carboxylic magnesium salts of this invention are to be added to a gasoline for an internal combustion engine, the amount added to the fuel may range from about 0.0001% to about 1.0% by weight. If, however, the basic magnesium salts are to be added to a gear lube or used in a diesel engine, hydraulic fluid, motor oil, etc., the amount may range as high as 25% by weight of the total composition. In some instances, even larger percentages, e.g., up to about 30% or higher by weight of the overbased magnesium carboxylic metal salts, may be utilized depending upon the particular use of the lubricant or fuel.

When used in lubricants or fuel, the salts of this invention are dissolved or stably dispersed in the media in question. The term "stably dispersed" as used in this specification and appended claims means a composition (e.g., a single additive or compound, a mixture of two or more additives or compounds, etc.) is dispersed in a given medium to an extent which allows it to function in its intended manner. Thus, for example, where a composition of this invention is used in an oil, it is sufficient that the composition be suspended in the oil in an amount sufficient to enable the oil to possess one or more of the desired properties imparted to it by the suspended composition. Such suspension of the compositions can be achieved in various conventional ways. For example, in constantly circulating oil or oil in splash lubricating systems, physical agitation can keep the compositions suspended in oil. Likewise, conventional dispersants (such as the acylated nitrogen dispersants disclosed in U.S. Pat. No. 3,219,666) often found in lubricating oils and fuels promote the stable dispersion or suspension of the composition. In any event, the intended compositions will be "soluble" or "stably dispersible" in the normally liquid media in which they will be used in at least the minimum concentrations set forth elsewhere herein. Thus, the terminology "soluble" and "stably dispersible" is used in a conventional manner and will be understood to those of ordinary skill in the art.

The salts of this invention can also be formulated into additive concentrates for use in fuels and lubricants. These concentrates contain, in addition to the salt, substantially inert solvent diluents, and, optionally, other additives as described herein.

As used in the specification and the appended claims, the term "substantially inert" when used to refer to solvents, diluents, base stocks, and the like, is intended to mean that the solvent, diluent, etc., is inert to chemical or physical change under the conditions which it is used so as not to materially interfere in an adverse manner with the preparation, storage, blending and/or functioning of the compositions, additive, compound, etc., of this invention in the context of its intended use. For example, small amounts of a solvent, diluent, etc., can undergo minimal reaction or degradation without preventing the making and using of the invention as described herein. In other words, such reaction or degradation, while technically discernible, would not be sufficient to deter the practical worker of ordinary skill in the art from making and using the invention for its intended purposes. "Substantially inert" as used herein is, therefore, readily understood and appreciated by those of ordinary skill in the art.

The additive concentrates of this invention contain about 10 to about 70% (by weight) of at least one substantially inert, organic solvent diluent and about 90 to about 30% of at least one magnesium salt.

The following illustrate oleaginous and fuel compositions of this invention.

EXAMPLE A

A lubricating composition is prepared by blending an SAE 10W-30 lubricating oil with 6.5% by weight of an acylated-nitrogen product obtained by reacting a high molecular weight polyolefin-substituted succinic acid with a polyamine, e.g., polyethylene polyamine, 1.28% by weight of a zinc dialkylphosphorodithioate, 0.005% by weight of a poly(alkylmethacrylate) anti-foam agent and 5.18% by weight of the basic carboxylic-magnesium salt obtained by the process of Example 1 of this invention.

EXAMPLE B

A blend is prepared with an SAE 10W-40 mineral lubricating oil, 1.0% by weight of the product of Example 1, 0.8% by weight of phosphorus as the adduct obtained by heating zinc dinonylphosphorodithioate with 0.25 mole of 1,2-hexene oxide at 120° C., 6% by weight of a polyisobutylene viscosity index improver having an average molecular weight of about 80,000; 0.005% by weight of a poly-(alkylmethacrylate) antifoam agent and 0.5% by weight of lard oil.

EXAMPLE C

A gasoline is blended with 0.001% by weight of the product of Example 12.

EXAMPLE D

A kerosene is blended with 0.1% by weight of the product of Example 6.

In addition to the basic magnesium salts of this invention, it is obvious that other known additives may be used in the fuel or lubricant. These additives include, for example, detergents of the ash-containing type, dispersants of the ashless type, viscosity-index improving agents, pour-point depressing agents, anti-foam agents, extreme-pressure agents, rust-inhibiting agents, oxidation and corrosion inhibiting agents and various mixtures of these materials in various proportions. More particularly, the ash-containing detergents may be illustrated by the oil soluble neutral and basic salts of the alkali or alkaline earth metals of the sulfonic acids, carboxylic acids or the organic phosphorus acids. An additive may be prepared, for example, by the reaction of an olefin polymer, e.g., polyisobutene, having a molecular weight of about 2000 with a phosphorizing agent including, for example, phosphorus trichloride, phosphorus heptasulfide, phosphorus pentasulfide, phosphorus trichloride and sulfur, white phosphorus and a sulfur halide or phosphorothioic chloride. The compositions most commonly used, however, are the salts of sodium, potassium, lithium, calcium, magnesium, strontium, barium and various mixtures thereof.

A method for preparing the basic salts comprises heating a mineral oil solution of the acid with a stoichiometric excess of a metal neutralizing agent, e.g., a metal oxide, hydroxide, carbonate, bicarbonate, sulfide, etc., at temperatures above about 50° C. In addition, various promoters may be used in the neutralizing process to aid in the incorporation of the excess of metal. These promoters are presently known and include compounds as the phenolic compounds, e.g., phenols, naphthols, alkylphenols, thiophenols, sulfurized alkylphenols and the various condensation products of formaldehyde with the phenolic compounds, e.g., alcohols such as methanol, 2-propanol, octyl alcohol, cellosolve, carbitol, ethylene glycol, stearyl alcohol and cyclohexyl alcohol; amines such as aniline, phenylenediamine, phenothiazine, phenyl-beta-naphthylamine and dodecylamine, etc. A particularly effective process for preparing the basic salts comprises mixing the acid with an excess of the alkaline earth metal in the presence of the phenolic promoter and a small amount of water and carbonating the mixture at an elevated temperature, e.g., 60° C. to about 200° C.

The extreme pressure agents, corrosion-inhibiting and oxidation-inhibiting agents are exemplified by the chlorinated aliphatic hydrocarbons such as chlorinated wax; organic sulfides and polysulfides such as benzyl disulfide, bis(chlorobenzyl)disulfide, dibutyl tetrasulfide, sulfurized sperm oil, sulfurized methyl ester of oleic acid, sulfurized alkylphenol, sulfurized dipentene, sulfurized terpene, etc.; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl-4-pentyl phenyl phosphite, polypropylene (molecular weight 500)-substituted phenyl phosphite, diisobutyl substituted phenyl phosphite; metal thiocarbamates such as zinc dioctyldithiocarbamate and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, the zinc salt of a phosphorodithioic acid produced by the reaction of phosphorus pentasulfide with an equimolar mixture of isopropyl alcohol and n-hexyl alcohol, etc.

The fuel or lubricating compositions may contain a metal detergent additive in amounts ranging from about 0.001% to about 15% by weight. In some applications, e.g., in lubricating marine diesel engines, the lubricating compositions may contain as much as 30% of a detergent additive. The compositions, e.g., lubricants or fuels, etc., may contain extreme pressure agents, viscosity-index improving agents, pour-point depressing agents, etc., each in amounts within the range of from about 0.001% to 15% and preferably in amounts of 0.1% to about 10%. One or more of the above-mentioned additives may be used either alone or in combination in various compositions, e.g., fuels or lubricating oils, with about 0.0001% to about 25% or 30% by weight of the basic carboxylic metal salts of this invention.

The oleaginous materials, e.g., lubricants and fuels, include animal and vegetable oils, e.g., castor oil, lard oil, etc., as well as solvent-refined or acid-refined mineral lubricating oils of the paraffinic, naphthenic or mixed paraffinic-naphthenic types. Oils of lubricating viscosity derived from coal or shale are useful base oils. The synthetic lubricating oils include the hydrocarbon oils and halo-substituted hydrocarbon oils such as polymerized and interpolymerized olefins (e.g., polybutylenes, propyleneisobutylene copolymers, chlorinated polybutylenes, etc.); alkylbenzenes (e.g., dodecylbenzene, tetradecylbenzene, dinonylbenzene, di-(2-ethylhexyl)benzene, etc.); polyphenyls (e.g., biphenyls, terphenyls, etc.) and the like. The alkylene oxide polymers and interpolymers and derivatives thereof where the terminal hydroxyl groups have been modified by esterification, etherification, etc., comprise another class of known synthetic lubricating oils. These are exemplified by the oils prepared by polymerization of ethylene oxide, propylene oxide, the alkyl and aryl ethers of these polyoxyalkylene polymers, e.g., methylpolyisopropylene glycol ether having an average molecular weight of 1000, diphenyl ether of polyethylene glycol having a molecular weight of 500 to 1000, diethyl ether of polypropylene glycol having a molecular weight of 1000 to 1500, etc., or mono- and polycarboxylic esters thereof, for example, the acetic acid esters, mixed $C_3$–$C_8$ fatty acid esters or the $C_{13}$Oxo acid diester of tetraethylene glycol, etc.

Other synthetic lubricating oils comprise the esters of dicarboxylic acids (e.g., phthalic acid, succinic acid, maleic acid, azelaic acid, suberic acid, sebacic acid, fumaric acid, adipic acid, linoleic acid dimer, etc.) with a variety of alcohols (e.g., butyl alcohol, hexyl alcohol, dodecyl alcohol, 2-ethylhexyl alcohol, pentaerythritol, etc.). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of 2-ethylhexanoic acid and the like.

Silicone-based oils such as the polyalkyl-, polyaryl-, polyalkoxy- or polyaryloxy-siloxane oils and silicate oils comprise another class of synthetic lubricants (e.g., tetraethyl-silicate, tetraisopropyl-silicate, tetra-(2-ethylhexyl)-silicate, tetra-(4-methyl-2-tetraethyl)-silicate, tetra-(p-tert-butylphenyl)-silicate, hexyl-(4-methyl-2-pentoxy)-disiloxane, poly(methyl)-disiloxanes, poly-(methyl-phenyl)-siloxanes, etc.). Other synthetic lubricants include the liquid esters of phosphorus-containing acids (e.g., tricresyl phosphate, trioctyl phosphate, diethyl ester of decane phosphonic acid, etc.), polymeric tetrahydrofurans and the like.

While this invention is described with a number of specific embodiments, it is obvious that there are other variations and modifications which can be made without departing from the spirit and scope of the invention as particularly set forth in the appended claims.

What is claimed is:

1. A process for preparing a noncarbonated, basic magnesium salt of a substituted hydroxy-containing aromatic carboxylic acid having a magnesium content of at least 150% and up to about 250% of the stoichiometrically equivalent amount, based on the total amount of acid present, which consists essentially of reacting at a temperature of about 25° C. up to the decomposition temperature of a reactant, in the absence of any inorganic acid material
   (A) at least one hydrocarbyl-substituted or substantially hydrocarbyl-substituted aromatic hydroxy carboxylic acid, salt or saponifiable derivative thereof, wherein the substantially hydrocarbon substituent contains up to about 10 weight percent of polar groups selected from the group consisting of mercapto, halogen, nitro, amino, nitroso, sulfo, keto, oxo groups and various combinations thereof, and;
   (B) a stoichiometric excess of at least one basically reactive magnesium compound selected from the group consisting of magnesium oxides, hydroxides and alkoxides for each equivalent of said acid salt or derivative thereof, in the presence of
   (C) at least about 0.1 mole of water for each equivalent of magnesium compound, and then refluxing the resulting mixture for a least about 0.5 hour with the proviso that the reaction is carried out in the absence of any carboxylic acid other than (A).

2. A fuel or lubricant composition comprising a major about of lubricating oil or normally liquid fuel and about 0.0001% to about 30% by weight of the total composition of the non-carbonated magnesium salt made by the process of claim 1.

3. A non-carbonate magnesium salt made by the process of claim 1.

4. An additive concentrate containing about 10 to about 70% of a substantially inert liquid organic solvent/diluent and about 90 to about 30% of at least one magnesium salt of claim 31.

5. The process claimed in claim 1 wherein the aromatic acid contains a hydrocarbyl substituent which is an aliphatic substituent of at least 8 carbon atoms.

6. A fuel or lubricant composition comprising a major amount of lubricating oil or normally liquid fuel and about 0.0001% to about 30% by weight of the total composition of the non-carbonated magnesium salt made by the process of claim 5.

7. A non-carbonated magnesium salt made by the process of claim 5.

8. An additive concentrate containing about 10 to about 70% of a substantially inert liquid organic solvent/diluent and about 90 to about 30% of at least one magnesium salt of claim 7.

9. The process claimed in claim 5 wherein (A) is a substituted salicylic acid or derivative thereof.

10. The process claimed in claim 9 wherein (A) is a magnesium salt.

11. The process claimed in claim 10 wherein the hydrocarbyl substitutent contains an average of about 12 to about 400 carbon atoms.

12. A fuel or lubricant composition comprising a major amount of lubricating oil or normally liquid fuel and about 0.0001% to about 30% by weight of the total composition of the non-carbonated magnesium salt made by the process of claim 9.

13. A fuel or lubricant composition comprising a major amount of lubricating oil or normally liquid fuel and about 0.0001% to about 30% by weight of the total composition of the non-carbonated magnesium salt made by the process of claim 10.

14. A fuel or lubricant composition comprising a major amount of lubricating oil or normally liquid fuel and about 0.0001% to about 30% by weight of the total composition of the non-carbonated magnesium salt made by the process of claim 11.

15. A non-carbonated magnesium salt made by the process of claim 9.

16. A non-carbonated magnesium salt made by the process of claim 11.

17. An additive concentrate containing about 10 to about 70% of a substantially inert liquid organic solvent/diluent and about 90 to about 30% of at least one magnesium salt of claim 15.

18. An additive concentrate containing about 10 to about 70% of a substantially inert liquid organic solvent/diluent and about 90 to about 30% of at least one magnesium salt of claim 16.

19. A process for preparing a non-carbonated, basic magnesium salt of a substituted hydroxy-containing aromatic carboxylc acid having a magnesium content of at least 150% and up to about 250% of the stoichiometrically equivalent amount, based on the total amount of acid present, which consists essentially of reacting, at a temperature of about 25° C. up to the decomposition temperature of a reactant, in the absence of any inorganic acid material (A) at least one hydrocarbyl-substituted or substantially hydrocarbyl-substituted aromatic hydroxy carboxylic acid, salt or saponifiable derivative thereof, wherein the substantially hydrocarbon substituent contains up to about 10 weight percent of polar groups selected from the group consisting of mercapto, halogen, nitro, amino, nitroso, sulfo, keto, oxo groups and various combinations thereof, and;

(B) a stoichiometric excess of at least one basically reactive magnesium compound selected from the group consisting of magnesium oxides, hydroxides and alkoxides for each equivalent of said acid salt or derivative thereof, in the presence of (C) at least about 0.1 mole of water for each equivalent of magnesium compound, and then refluxing the resulting mixture for at least about 0.5 hour with the proviso that the reaction is carried out in the absence of any carboxylic acid other than (A); wherein the reaction of (A), (B) and (C) is in the presence of (D) about 0.05 to about 0.25 equivalent for each equivalent of aromatic acid (A) of at least one sulfur-containing organic acid, and in the absence of any organic acid other than (A) and (D).

20. A process as claimed in claim 19 wherein the sulfur-containing acid is a sulfonic acid.

21. The process as claimed in claim 20 wherein the aromatic hydroxy carboxylic acid (A) contains a hydrocarbyl substituent of at least 8 aliphatic carbons.

22. The process as claimed in claim 21 wherein the aromatic hydroxy carboxylic acid is a monohydroxy carboxylic acid.

23. The process as claimed in claim 21 further characterized wherein the substituted aromatic hydroxy carboxylic acid is a monocarboxylic acid.

24. The process as claimed in claim 23 wherein the aromatic hydroxy carboxylic acid is a substituted salicylic acid or a derivative thereof.

25. The process as claimed in claim 21 further characterized wherein a salt of the substituted aromatic hydroxy carboxylic acid is used.

26. The process as claimed in claim 25 wherein the metal salt is an alkali or alkaline earth metal salt.

27. The process as claimed in claim 26 wherein the salt is a magnesium salt.

28. A fuel or lubricant composition comprising a major amount of lubricating oil or normally liquid fuel and about 0.0001% to about 30% by weight of the total composition of the non-carbonated magnesium salt made by the process of claim 27.

29. A non-carbonated magnesium salt made by the process of claim 27.

30. An additive concentrate containing about 10 to about 70% of a substantially inert liquid organic solvent/diluent and about 90 to about 30% of at least one magnesium salt of claim 29.

31. The process claimed in claim 27 wherein the hydrocarbyl substituent contains an average of about 12 to about 400 carbon atoms.

32. A fuel or lubricant composition comprising a major amount of lubricating oil or normally liquid fuel and about 0.0001% to about 30% by weight of the total composition of the non-carbonated magnesium salt made by the process of claim 31.

33. A non-carbonated magnesium salt made by the process of claim 31.

34. An additive concentrate containing about 10 to about 70% of a substantially inert liquid organic solvent/diluent and about 90 to about 30% of at least one magnesium salt of claim 33.

35. The process as claimed in claim 21 wherein the saponifiable derivative (A) is selected from the group consisting of organic acid anhydrides, esters and halides.

36. The process as claimed in claim 35 further characterized wherein (A) is a hydrocarbon-substituted salicylic acid magnesium salt.

37. A fuel or lubricant composition comprising a major amount of lubricating oil or normally liquid fuel and about 0.0001% to about 30% by weight of the total composition of the non-carbonated magnesium salt made by the process of claim 21.

38. A non-carbonated magnesium salt made by the process of claim 21.

39. An additive concentrate containing about 10 to about 70% of a substantially inert liquid organic solvent/diluent and about 90 to about 30% of at least one magnesium salt of claim 38.

40. The process claimed in claim 21 wherein the hydrocarbyl substituent contains an average of about 12 to about 400 carbon atoms.

41. The process claimed in claim 40 wherein the water is present in an amount ranging from about 0.1 to about 10 moles for each equivalent of said magnesium compound.

42. A fuel or lubricant composition comprising a major amount of lubricating oil or normally liquid fuel and about 0.0001% to about 30% by weight of the total composition of the non-carbonated magnesium salt made by the process of claim 41.

43. A non-carbonated magnesium salt made by the process of claim 41.

44. An additive concentrate containing about 10 to about 70% of a substantially inert liquid organic solvent/diluent and about 90 to about 30% of at least one magnesium salt of claim 43.

* * * * *